(12) United States Patent
Wells et al.

(10) Patent No.: US 9,314,616 B2
(45) Date of Patent: Apr. 19, 2016

(54) TEMPORARY IMPLANTABLE MEDICAL ELECTRICAL LEADS

(75) Inventors: Patrick D. Wells, Minneapolis, MN (US); Carole A. Tronnes, Stillwater, MN (US)

(73) Assignee: Medtronic, Inc., Minneapolis, MN (US)

(*) Notice: Subject to any disclaimer, the term of this patent is extended or adjusted under 35 U.S.C. 154(b) by 1193 days.

(21) Appl. No.: 13/084,420

(22) Filed: Apr. 11, 2011

(65) Prior Publication Data

US 2011/0257500 A1  Oct. 20, 2011

Related U.S. Application Data

(60) Provisional application No. 61/324,144, filed on Apr. 14, 2010.

(51) Int. Cl.
  *A61N 1/00* (2006.01)
  *A61N 1/05* (2006.01)
  *A61B 5/04* (2006.01)

(52) U.S. Cl.
  CPC ............ *A61N 1/0551* (2013.01); *A61N 1/0558* (2013.01); *Y10T 29/49204* (2015.01)

(58) Field of Classification Search
  CPC ............ A61B 5/0024; A61B 18/1492; A61B 5/6852; A61B 5/0478; A61N 1/0573; A61N 1/059; A61N 1/057; A61N 1/3956; A61N 1/0488
  USPC ................. 600/372, 373–378, 381, 393, 424, 600/508–510; 607/7, 9, 28, 119, 122–123, 607/126–131
  See application file for complete search history.

(56) References Cited

U.S. PATENT DOCUMENTS

| | | | |
|---|---|---|---|
| 4,711,027 A | 12/1987 | Harris | |
| 5,456,707 A | 10/1995 | Giele | |
| 6,126,654 A * | 10/2000 | Giba | A61B 18/24 604/511 |
| 6,251,107 B1 * | 6/2001 | Schaer | A61B 18/1492 600/374 |
| 6,360,130 B1 | 3/2002 | Duysens et al. | |
| 6,501,992 B1 | 12/2002 | Belden et al. | |
| 6,687,538 B1 | 2/2004 | Hrdlicka et al. | |
| 6,757,970 B1 | 7/2004 | Kuzma et al. | |
| 7,158,837 B2 | 1/2007 | Osypka et al. | |
| 7,277,762 B2 | 10/2007 | Belden et al. | |
| 7,280,875 B1 * | 10/2007 | Chitre et al. | 607/122 |

(Continued)

FOREIGN PATENT DOCUMENTS

EP 815897 12/2004
WO WO93/09840 5/1993

*Primary Examiner* — Joseph Stoklosa
*Assistant Examiner* — Brian M Antiskay (57) ABSTRACT

A temporary implantable medical electrical lead includes a conductor extending along a proximal, extracorporeal length and a distal, subcutaneous length of the lead. Electrically isolated first and second wire filars of the conductor are wound to form an elongate lumen of the lead. First and second electrodes are mounted directly onto the conductor, along the subcutaneous length, and each is directly coupled to the corresponding filar. A fixation member is attached to a tubular member, which is conformed to an outer surface of the conductor so as to only cover the conductor along the subcutaneous length, leaving the outer surface exposed along a portion thereof, adjacent to the extracorporeal length. When the lead is implanted, the fixation member holds the subcutaneous length in a relatively fixed location, and fluid communication exists between the outer surface of the conductor and the lumen of the lead.

14 Claims, 5 Drawing Sheets

(56) References Cited

U.S. PATENT DOCUMENTS

| | | |
|---|---|---|
| 7,493,159 B2 | 2/2009 | Hrdlicka et al. |
| 2003/0045919 A1* | 3/2003 | Swoyer ............... A61N 1/0558 607/122 |
| 2004/0162600 A1* | 8/2004 | Williams .................. 607/122 |
| 2004/0260375 A1* | 12/2004 | Zhang .................. A61N 1/056 607/126 |
| 2006/0095107 A1* | 5/2006 | Osypka ..................... 607/122 |
| 2007/0100411 A1* | 5/2007 | Bonde ................ A61N 1/0558 607/126 |
| 2007/0255370 A1* | 11/2007 | Bonde et al. ............... 607/117 |
| 2007/0293924 A1* | 12/2007 | Belden et al. ............. 607/122 |
| 2008/0046059 A1 | 2/2008 | Zarembo et al. |
| 2010/0137928 A1* | 6/2010 | Duncan et al. ................ 607/5 |

* cited by examiner

TEMPORARY IMPLANTABLE MEDICAL ELECTRICAL LEADS

The present application claims priority to U.S. Provisional Patent Application No. 61/324,144, filed Apr. 14, 2010, which application is hereby incorporated by reference as if re-written in its entirely.

TECHNICAL FIELD

The present disclosure pertains to temporary implantable medical electrical leads, and more particularly to the design and assembly thereof.

BACKGROUND

Temporary implantable medical electrical leads are often employed to evaluate the efficacy of electrical stimulation prior to implanting a chronically implantable stimulation system within a patient. For example, the efficacy of sacral nerve stimulation in patients, for the treatment of urinary incontinence, is evaluated with what is known as trialing or a percutaneous nerve evaluation (PNE) lead, which is temporarily implanted, via a minimally invasive procedure, for an evaluation period, for example, of up to approximately 7 days, depending upon the particular patient. Implant access to the sacral nerves is typically gained via fluoroscopic and/or ultrasound guidance of a spinal needle that is percutaneously inserted, from a posterior side of the sacrum, through a foramen thereof and into the region of the sacral nerves; the PNE lead is then inserted through a lumen of the needle such that a stimulating electrode of the lead contacts a sacral nerve.

Figure 1:
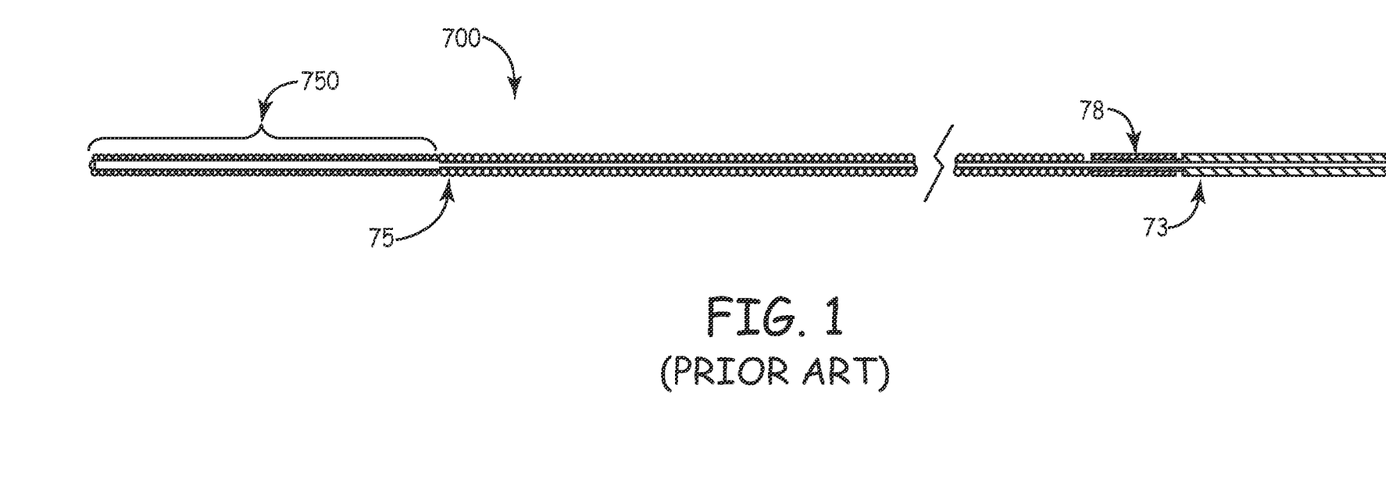
FIG. 1 is a cross-section view of the unipolar prior art lead.

An example of a PNE lead, which is known in the art, is shown in the section view of FIG. 1. FIG. 1 illustrates a unipolar PNE lead 700 that includes a conductor coil 75 formed from a single wire filar would around a lumen of lead 700. The wire filar is preferably formed as a cable, by a plurality of wire strands, for example, seven wire strands, that are braided together; and the wire filar has an insulative coating, for example, formed from a fluoropolymer material, that provides electrical isolation along a majority of the length of conductor 75. The insulative coating is removed from the wire filar along a distal length of conductor 75 to form a stimulating electrode 750 of lead 700. The insulative coating is also removed from the wire filar at a proximal end of coil 75, where a junction/coupling is formed with a connector 73 of lead 700. According to FIG. 1, the coupling is enclosed within a tubular member 78, which may be formed from a heat shrinkable polymer material, such as polyester.

When lead 700 is temporarily implanted in a patient, for example, such that electrode 750 contacts a sacral nerve, and when a ground pad is coupled to the patient's epidermis, connector 73, which remains extracorporeal (outside the patient's body), may be coupled to a stimulation source in order to deliver unipolar stimulation to the nerve via electrode 750. If stimulation from lead 700 is found effective for a particular placement of electrode 750 in the patient, lead 700 is replaced with a chronically implantable lead that is part of a chronically implantable system. Examples of such a chronically implantable lead include the Model 3093 and the Model 3889, both of which are quadripolar leads available from Medtronic, Inc.

Although the prior art lead 700 has been found useful, there remains a need for new and improved designs of temporary implantable medical electrical leads.

BRIEF DESCRIPTION OF THE DRAWINGS

The following drawings are illustrative of particular exemplary embodiments and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements.

DETAILED DESCRIPTION

The following detailed description is exemplary in nature and is not intended to limit the scope, applicability, or configuration of embodiments disclosed herein. Rather, the following description provides practical illustrations for implementing exemplary embodiments. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

Figure 2:
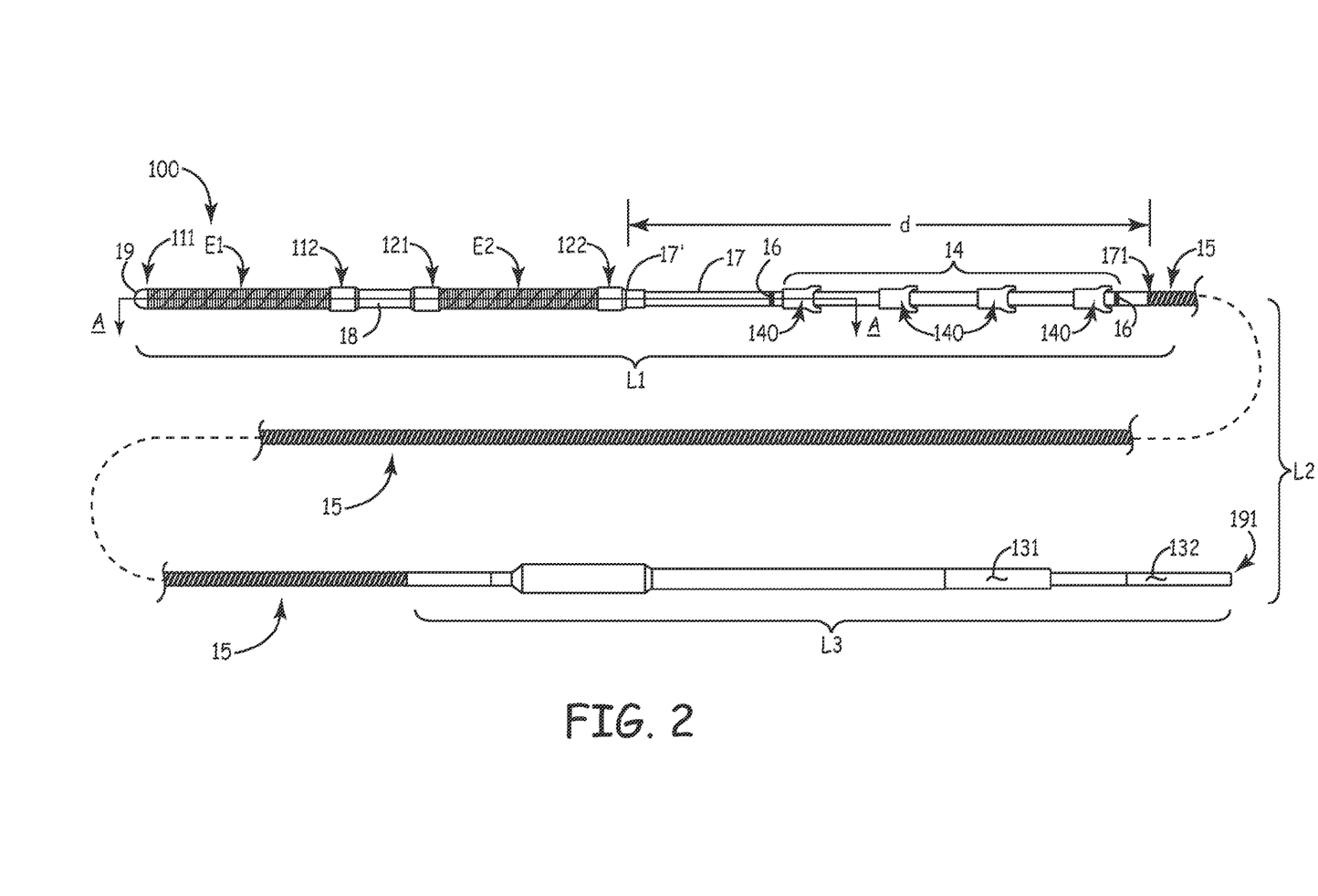
FIG. 2 is a plan view of a temporary implantable medical electrical lead, according to some embodiments of the present invention.
Figure 3:
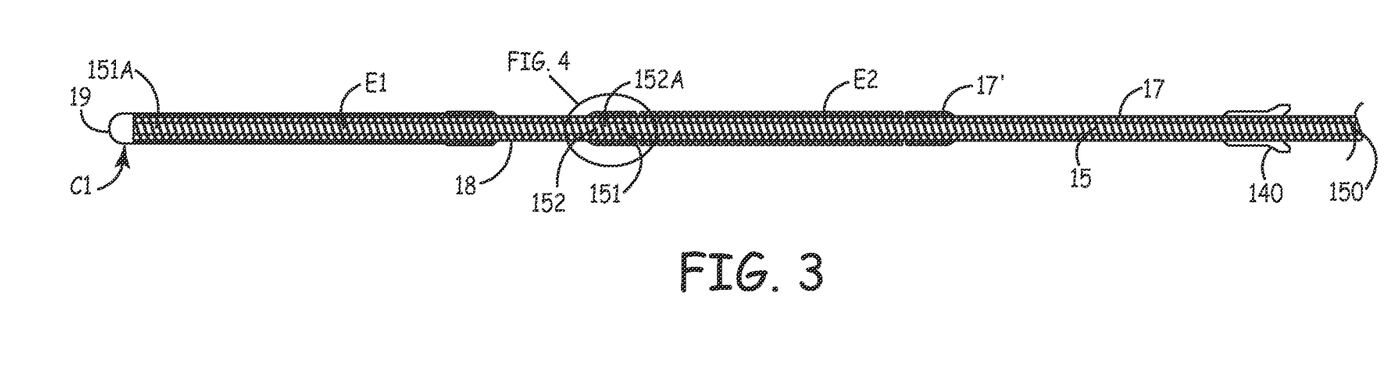
FIG. 3 is a section view through section line A-A of FIG. 2, according to some embodiments.

FIG. 2 is a plan view of a temporary implantable medical electrical lead 100, according to some embodiments of the present invention. Dashed lines in FIG. 2 represent the extent of lead 100 between elongate sections thereof. FIG. 2 illustrates lead 100 having a first length L1 and a second length L2; first length L1 may be characterized as a distal, subcutaneous length, a majority of which, if not all, will be contained within a body of a patient when lead 100 is implanted; and second length L2 may be characterized as a proximal, extracorporeal length, which will remain outside the body of the patient when lead 100 is implanted. FIG. 2 further illustrates lead 100 including a conductor coil 15, a first electrode coil E1, a second electrode coil E2, a tubular member 17 and a fixation member 14 attached to tubular member 17. First and second electrodes E1, E2 are shown spaced apart from one another along distal, subcutaneous length L1 of lead 100. With reference to FIG. 3, which is a section view through line A-A of FIG. 2, according to some embodiments, electrode coils E1, E2 are shown mounted directly onto conductor coil 15. Electrode coils E1, E2 are preferably formed by a wound Pt/Ir alloy wire, but other suitable wire materials, such as stainless steel, may be employed, according to alternate embodiments.

Figure 4:
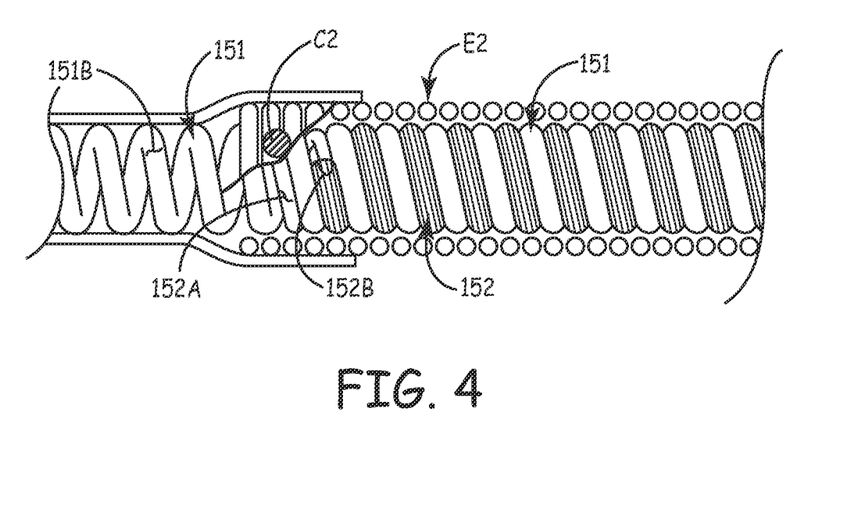
FIG. 4 is a detail view of a portion of the lead shown in FIG. 3, according to some embodiments.

With further reference to FIGS. 3 and 4, conductor coil 15 is shown including first wire filar 151 and a second wire filar 152, which are wound to form an elongate lumen 150 of lead 100 that extends along both lengths L1 and L2. Although each wire filar 151, 152 may be formed from a single wire, each filar 151, 152 is preferably formed as a cable, from a plurality of wire strands braided together, according to methods known to those skilled in the art; and, according to the illustrated embodiment, each wire filar 151, 152 has an insulative coating 151B, 152B, respectively, for electrical isolation, and a portion 151A, 152A from which coating 151B, 152B is removed for direct electrical coupling with the corresponding electrode E1, E2. According to an exemplary embodiment, each of wire filars 151, 152 is a cable that has a diameter of approximately 0.25 mm (0.01 inch), and that includes seven braided wire strands of a stainless steel alloy (304L or 316L), wherein each strand has a diameter of approximately 0.05 mm (0.002 inch); and each insulative coating 151B, 152B is ethylene tetrafluoroethylene (ETFE). However, a number suitable alternatives for wire filars 1511, 152 and insulative coatings 151B, 152B are known to those skilled in the art. Coating 151B, 152B may be removed from respective portions 151A, 152A by any suitable method known to those skilled in the art, for example, mechanical stripping or laser ablation.

Although not shown, it should be understood that each wire filar 151, 152 is also electrically coupled to a corresponding contact 131, 132 of a connector 13 that terminates the proximal end of lead 100. Contacts 131, 1132 provide for bipolar electrical connection of electrodes E1, E2 to an extracorporeal stimulation source, and lumen 150 extends through connector 13 to a proximal-most end 191 of lead 100 in order to provide passage for a stylet (not shown) that, when inserted within lumen 150, is used to help push distal length L1 of lead 100 into a subcutaneous implant position.

FIG. 3 further illustrates a distalmost tip 19 of lead 100 being formed by a direct electrical coupling C1 of portion 151A of first wire filar 151 to first electrode coil E1 in proximity to a distal end 111 thereof (FIG. 2); and FIGS. 3 and 4 further illustrates a direct electrical coupling C2 of portion 152A of second wire filar 152 to second electrode coil E2 being located in proximity to a distal end segment 1211 (FIG. 2) of second electrode E2. Although direct coupling C2 is shown located in proximity to distal end segment 121, it should be understood that embodiments of the invention are not so limited and that portion 152A of second wire filar 152 may be located anywhere along the length of electrode coil E2 for direct coupling to any portion of electrode coil E2. Furthermore, portion 152A need not be at a distal end of second wire filar 152, as illustrated, but could be offset proximally from the distal end of second wire filar 152. According to preferred embodiments, direct couplings C1, C2 are formed by laser welding, via methods known to those skilled in the art; alternately plasma welding or resistance welding, methods of which are also known in the art, may be employed.

Figure 5:
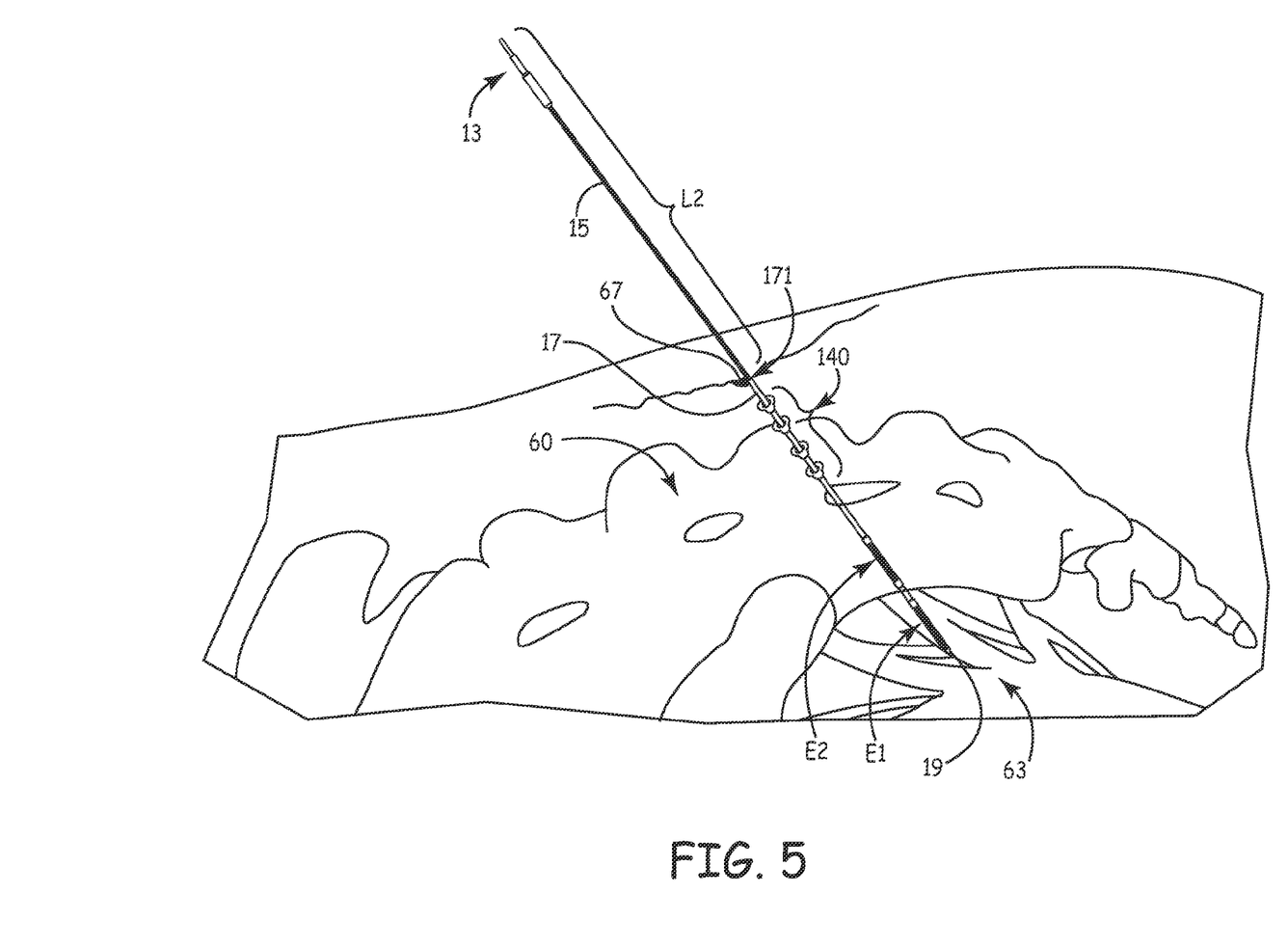
FIG. 5 is a schematic showing an implanted lead, according to some embodiments.

With further reference to FIGS. 2 and 3, tubular member 17 is shown closely conforming to an outer surface of conductor coil 15 to cover conductor coil 15 only along distal, subcutaneous length L1, proximal to second electrode E2. FIGS. 2 and 3 further illustrate fixation member 14 including a plurality of tine elements 140 spaced apart from one another along a length of tubular member 17, which length may be between approximately 12.7 mm (0.5 inch) and approximately 2.54 cm (one inch). According to the illustrated embodiment, fixation member 14 is configured to hold subcutaneous length L1 of lead 100 in a relatively fixed position, when lead 100 is implanted, for example, to stimulate sacral nerves 63, as is illustrated in the schematic of FIG. 5. With reference to FIG. 5, it should be understood that the sacrum 60, which overlays the sacral nerves 63, is overlaid with muscle tissue into which tine elements 140 may fixate to hold lead 100 in the illustrated position. Furthermore, tine elements 140 are preferably formed from a relatively flexible material so that tine elements 140 collapse toward an outer surface of tubular member 17, when lead 100 is inserted, for example, though a needle lumen for implant. According to some preferred embodiments, a profile of lead 100 is small enough for insertion through an 18 gauge needle (lumen ID approximately 1.12 mm (0.044 inch), such that a maximum outer diameter of lead 100 may be no greater than approximately 0.889 mm (0.035 inch), for example, along electrode coils E1, E2, although tine elements 140 may protrude to a larger diameter, when un-deformed. It should be noted that alternative configurations of fixation member 14 that are know in the art, for example hooks or barbs, may be employed by alternative embodiments of the present invention.

FIG. 2 further illustrates optional radiopaque markers 16, for example, Pt/Ir rings, located at either end of fixation member 14; one or both of markers 16 may be useful in the positioning of lead 100 during implant and/or during follow-up, if fluoroscopy is employed for visualization. If one or both of markers 16 are included in lead 100, one or both markers 16 are preferably mounted directly onto the external surface of conductor coil 15 and contained beneath tubular member 17; alternately, one or both of markers 16 may be mounted onto an external surface of tubular member 17.

With further reference to FIG. 5, in conjunction with FIG. 2, according to preferred embodiments of the present invention, a length of tubular member 17 is limited so that the outer surface of conductor coil 15 remains exposed just proximal to a proximal terminal end 171 of tubular member 17 and along a portion of subcutaneous length L1 of lead 100 that is adjacent to extracorporeal length L2. FIG. 5 illustrates proximal terminal end 171 of tubular member 17 positioned just beneath a subcutaneous access site 67 for lead 100, such that an exposed portion of the outer surface of coil, just proximal to end 171, can allow for tissue in-growth through coil 15 and into lumen 150, at access site 67. Thus, as a result of the limited length of tubular member 17, the fluid communication between the outer surface of conductor coil 15 and lumen 150 can help, by allowing tissue in-growth, to prevent lumen 150 from acting as a conduit for the potential spread of infection from the proximal, extracorporeal length L2 of lead 100 to the subcutaneous implant site during the implant evaluation period. According to some exemplary embodiments, with reference to FIG. 2, a distance d between a proximal end segment 122 of second electrode coil E2 and proximal terminal end 171 of tubular member 17 is no greater than approximately 2.54 cm (one inch).

FIGS. 2 and 3 illustrate a distal section 172 of tubular member 17 overlapping proximal end segment 122 of second electrode coil E2. According to some embodiments, distal section 172 is an integral extension of tubular member 17, which is conformed to an outer surface of proximal end segment 122 of second electrode E2 at the same time that tubular member 17 is conformed to the outer surface of conductor coil 15; according to some alternate embodiments, distal section 172 is initially separate from tubular member 17 and overlaps both tubular member 17 and proximal end segment 122 of second electrode E2 for a conforming fit thereover. FIGS. 2 and 3 further illustrate another tubular member 18 that closely conforms to the outer surface of conductor coil 15 between first and second electrode coils E1, E2, and that overlaps a proximal end segment 112 of first electrode coil E1 and distal end segment 121 of second electrode E2. According to some preferred embodiments, tubular member 18 is formed from the same material as tubular member 17 and distal section 172, and is conformed to coils 15, E1, E2 by a similar process, examples of which will be described in conjunction with FIG. 6, below. With reference to FIG. 4, according to some embodiments, direct coupling C2 is located beneath the overlapping of tubular member 18 at distal end segment 121 of second electrode coil E2. According to alternate embodiments, portion 152A of second wire filar 152 is located in proximity to proximal end segment 122 of second electrode coil E2, such that direct coupling C2 is made of portion 152A to proximal end segment 122 and is, thus, located beneath the overlapping of distal section 172 at proximal end segment 122. It may be appreciated that the overlapping of distal section 172 and the overlapping of tubular member 18 are useful to contain respective end segments 122, 121 and 112 of electrode coils E2, E1, as well as couplings C1, C2, in the illustrated embodiment, and thereby lend additional structural integrity to lead 100.

Returning to FIG. 5, first electrode E1 of lead 100 is shown positioned for stimulating contact with one of sacral nerves 63, so that bipolar stimulation between electrodes E1, E2 can be evaluated. Alternatively, second electrode E2 may serve as the stimulating electrode for evaluation of an opposite polarity of bipolar stimulation, either with lead 100 located in the illustrated position, or having been re-positioned. It should be noted that the bipolar stimulation afforded by lead 100, as compared to the unipolar stimulation provided by the prior art lead 700 (FIG. 1), is more focused and better simulates the potential chronic stimulation from a multi-polar chronically implanted lead (i.e. either one of the aforementioned Models 3093 and 3889). Furthermore, the two electrodes E1, E2 provide more options for the investigation of alternate types of stimulation to determine the efficacy of electrical stimulation therapy in various patients.

Figure 6:
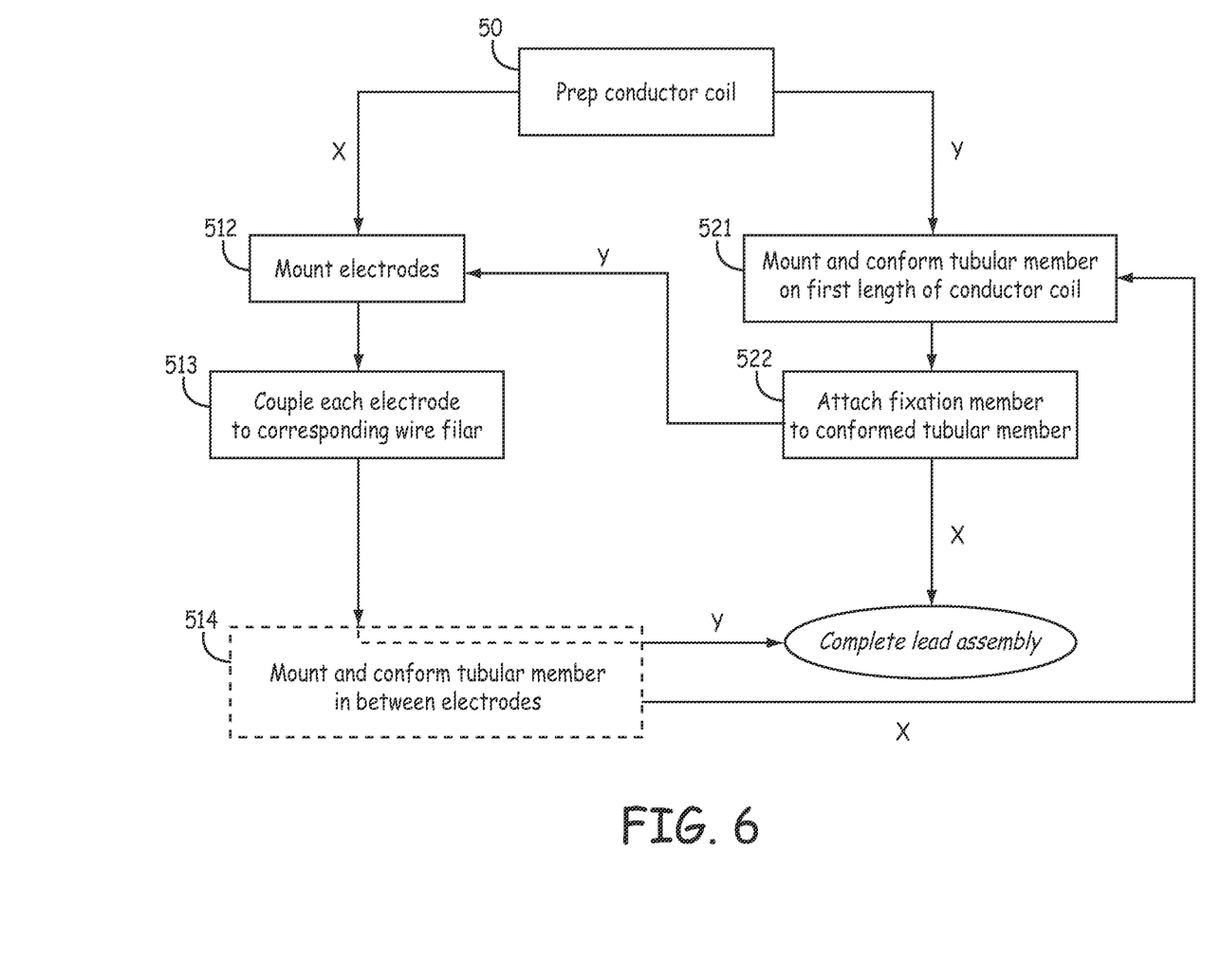
FIG. 6 is a flow chart outlining some assembly methods of the present invention.

Turning now to FIG. 6, some assembly methods of the present invention will be described with reference to lead 100. FIG. 6 illustrates an initial step 50 of an assembly method for lead 100 wherein conductor coil 15 is prepared. According to some preferred methods, after first and second wire filars 151, 152 are coated with an insulative coating, such as ETFE or another suitable insulative material, filars 151, 152 are wound into coil 15 such that lumen 150 extends along the length, preferably the entire length, of coil 15 and each end of filars is positioned for electrical coupling to the corresponding electrode E1, E2 and connector contact 131, 132. Preparing conductor coil 15, per step 50, also involves the removal of the insulative coating from the ends of filars 151, 152, preferably after winding, to allow for electrical coupling. Alternately, the insulative coating may be removed from portions of filars 151, 152 that are offset from the ends thereof. Insulation removal may be performed by mechanical stripping, laser ablation or any other suitable method know to those skilled in the art. Following step 50, either of paths X and Y may be followed, according to various alternative methods. According to some methods, per path X, a sequence proceeds from a step 512 to a step 513, then, optionally, to a step 514, before proceeding to steps 521 and 522. According to some methods, per path Y, a sequence of assembly steps proceeds from step 521 to step 522 and then to step 512 followed by step 513 and, optionally step 514. It should be noted that these steps of paths X and Y pertain primarily to the first or distal, subcutaneous length L1 of lead 100, and that the assembly of connector 13, at proximal end of the second or proximal, extracorporeal length L2 may be performed either prior to or following these steps. Each of the aforementioned steps, according to some preferred methods, is described in greater detail below.

In step 512 each of electrodes E1 and E2 is mounted on conductor coil 15 such that the electrodes are spaced apart from one another along distal length L1. After mounting, per step 512, each electrode E1, E2 is directly electrically coupled, per step 513, to the corresponding wire filar 151, 152 of conductor coil 15 (portions 151A, 152A), for example, via laser welding. According to some preferred methods, distal end 111 of mounted first electrode coil E1 is welded to portion 151A of first wire filar 151, for example, to form distal tip 19. According to step 521, tubular member 17 is mounted and conformed to conductor coil 15 either before steps 512 and 513 (path Y) or after steps 512 and 513 (path X). According to some methods, if distal section 172 of tubular member, which overlaps proximal end segment 122 of first electrode coil E1, is integral with tubular member 17, distal section 172 is simultaneously conformed to proximal end segment 122 in step 521. Alternately, if distal section 172 is initially separate from tubular member 17, section 172 is mounted on conductor coil 15 so as to overlap both conformed tubular member 17 and proximal end segment 122 of second electrode E2 prior to being, conformed thereto.

Tubular member 17 (including distal section 172) is preferably formed from a heat shrinkable material having a relatively thin wall, for example, between approximately 0.008 mm (0.0003 inch) and approximately 0.001 inch (to maintain a relatively low profile of lead 100), and heating of tubular member 17 (including distal section 172), in order to conform member 17 (including distal section 172) to conductor coil 15, may be accomplished via the application of hot air, for example, from a hot air nozzle, or by any other suitable method known to those skilled in the art. A suitable example of a heat shrink material is polyester, for which biocompatible medical grades of shrink tubing are known to those skilled in the art. According to an exemplary embodiment, tubular member 17, distal section 172 and tubular member 18 (optional, per step 514—described below) are initially all separate pieces of polyester shrink tubing, and, prior to being conformed, tubular member 17 has an outer diameter of approximately 0.71 mm (0.028) inch and a wall thickness of approximately 0.025 mm (0.001 inch), each of distal section 172 and tubular member 18 has an outer diameter of approximately 0.038 inch and a wall thickness of approximately 0.01 mm (0.0005 inch). According to some alternate embodiments, tubular member 17, distal section 172 and tubular member 18 are formed from a polyurethane material or any other suitable biocompatible material that is relatively flexible and can be made to conform to coils 15, E1 and E2 according to the illustrated embodiment.

Once tubular member 17 has been conformed to conductor coil 15, a fixation member 14 is attached to tubular member 17, per step 522. According to some preferred embodiments, fixation member 14 includes tine elements 140, and, if tubular member 17 is polyester heat shrink tubing, elements 140 are preferably formed from a polyester copolymer and are attached to conformed tubular member 17 by thermal bonding. Alternatively, or in addition, an adhesive material can be used to attached tine elements 140 to conformed tubular member 17. It should be noted that step 521 and/or step 522 may fall in between steps 512 and 513, according to some alternate methods.

According to some preferred methods, another tubular member 18 is mounted onto conductor coil 15 and conformed to thereto in between mounted and coupled electrodes E1, E2, per optional step 514. Opposing ends of the other tubular member 18 preferably overlap the respective proximal end segment 112, of first electrode E1, and distal end segment 121 of second electrode E2, so that tubular member 18 is also conformed to end segments 112, 121, per optional step 514. According to preferred embodiments, tubular member 18 is formed from the same material that forms tubular member 17 so that the same methods can be employed for conforming both of tubular members 17, 18.

In the foregoing detailed description of the disclosure, specific exemplary embodiments of the invention have been described. However, it may be appreciated that various modifications and changes can be made, without departing from the scope of the disclosure, as set forth in the appended claims.

We claim:

1. A temporary implantable medical electrical lead having a proximal, extracorporeal length and a distal, subcutaneous length, the lead comprising:
 a conductor coil including a plurality of wire filars being wound to form an elongate lumen that extends along the extracorporeal and subcutaneous lengths of the lead, each wire filar of the plurality of wire filars being electrically isolated by an insulative coating thereof, but each wire filar including a portion from which the insulative coating is removed, the portion of a first wire filar of the plurality being spaced apart, distally, from the portion of a second wire filar of the plurality along the subcutaneous length of the lead;
 a first electrode coil mounted directly onto the conductor coil along the subcutaneous length of the lead;
 a first direct electrical coupling being a weld between a distal end of the first electrode coil and the portion of the first wire filar from which the insulative coating thereof is removed, the weld forming a distalmost tip of the lead;
 a second electrode coil mounted directly onto the conductor coil along the subcutaneous length of the lead, the second electrode coil being spaced apart, proximally, from the first electrode coil;
 a second direct electrical coupling between the second electrode coil and the portion of the second wire filar from which the insulative coating thereof is removed;
 a tubular member closely conforming to an outer surface of the conductor coil to cover the conductor coil only along the subcutaneous length of the lead, the tubular member including a proximal terminal end, the tubular member extending proximally from the second electrode coil to the proximal terminal end, and the electrically isolated plurality of wire filars of the conductor coil being exposed along a portion of the subcutaneous length of the lead, the portion of the subcutaneous length extending proximally from the proximal terminal end of the tubular member and being adjacent to the extracorporeal length of the lead, the electrically isolated plurality of wire filars, exposed along the portion of the subcutaneous length, allowing fluid communication between the outer surface of the conductor coil and the lumen, and the portion of the subcutaneous length being free of any electrode surface; and
 a fixation member attached to the tubular member, the fixation member being configured to hold the subcutaneous length of the lead in a relatively fixed position, when the lead is implanted.

2. The lead of claim 1, further comprising another tubular member, which closely conforms to the outer surface of the conductor coil between the first and second electrodes, and which overlaps a proximal end segment of the first electrode coil and a distal end segment of the second electrode coil.

3. The lead of claim 2, wherein the second direct electrical coupling between the second electrode coil and the portion of the second wire filar, from which the insulative coating thereof is removed, is located beneath the overlapping of the other tubular member that conforms to the outer surface of the conductor coil between the first and second electrodes.

4. The lead of claim 1, wherein the second direct electrical coupling between the second electrode coil and the portion of the second wire filar, from which the insulative coating thereof is removed, is located in proximity to a proximal end of the second electrode coil.

5. The lead of claim 1, wherein the second direct electrical coupling between the second electrode coil and the portion of the second wire filar, from which the insulative coating thereof is removed, is located in proximity to a distal end of the second electrode coil.

6. The lead of claim 1, wherein the tubular member overlaps a proximal end segment of the second electrode.

7. The lead of claim 6, wherein the second direct electrical coupling between the second electrode coil and the portion of the second wire filar, from which the insulative coating thereof is removed, is located beneath the overlapping of the tubular member.

8. The lead of claim 1, wherein the fixation member comprises a plurality of tine elements spaced apart from one another along a length of the tubular member.

9. The lead of claim 8, wherein the length over which the tine elements are spaced is between approximately 12.7 mm (0.5 inch) and approximately one inch.

10. The lead of claim 8, wherein the tubular member and the plurality of tine elements comprise polyester.

11. The lead of claim 1, further comprising a radiopaque marker attached to the subcutaneous length of the lead either just proximal or just distal to the fixation member.

12. The lead of claim 11, wherein the radiopaque marker is mounted onto the external surface of the coil and contained beneath the tubular member.

13. The lead of claim 1, wherein a distance between a proximal end segment of the second electrode and the proximal terminal end of the tubular member is no greater than approximately 2.54 cm (1 inch).

14. The lead of claim 1, wherein the tubular member has a wall thickness less than approximately 0.05 mm (0.002 inch).

* * * * *